United States Patent [19]
Frost et al.

[11] Patent Number: 5,629,181
[45] Date of Patent: *May 13, 1997

[54] SYNTHESIS OF CATECHOL FROM BIOMASS-DERIVED CARBON SOURCES

[75] Inventors: John W. Frost; Karen M. Draths, both of West Lafayette, Ind.

[73] Assignee: Purdue Research Foundation, West Lafayette, Ind.

[*] Notice: The portion of the term of this patent subsequent to Dec. 1, 2009, has been disclaimed.

[21] Appl. No.: 122,919

[22] Filed: Sep. 16, 1993

[51] Int. Cl.$^6$ .............................. C12P 7/22; C12P 1/04; C12N 15/09
[52] U.S. Cl. .................. 435/156; 435/170; 435/172.3
[58] Field of Search .................... 435/155, 69.1, 435/170, 156, 252.3, 252.33, 320.1, 849, 852, 172.3; 536/23.1, 23.2

[56] References Cited

U.S. PATENT DOCUMENTS

| | | |
|---|---|---|
| 3,970,522 | 7/1976 | Sasajima et al. ............ 435/105 |
| 4,681,852 | 7/1987 | Tribe ............................ 435/108 |
| 4,753,883 | 6/1988 | Backman et al. ............ 435/232 |
| 4,908,312 | 3/1990 | Ozaki et al. .................. 435/108 |
| 5,017,481 | 5/1991 | Matsui et al. ................ 435/108 |
| 5,168,056 | 12/1992 | Frost ............................ 435/172.3 |
| 5,272,073 | 12/1993 | Frost et al. .................. 435/155 |

OTHER PUBLICATIONS

Bailey (1991) Science, vol. 252, pp. 1668–1675.
A.J. Pittard, "Biosynthesis of the Aromatic Amino Acids", in Escherichia coli & Salmonella typhimurium, Editor in Chief: F.C. Neidhardt, American Soc. for Microbiology, Washington, pp. 368–394, 1987.
K.M. Herrmann et al., "The Common Aromatic Biosynthetic Pathway" in Amino Acids: Biosynthesis and Genetic Regulation, Addison–Wesley Reading, pp. 301–376, 1983.
K.M. Draths et al. "Synthesis Using Plasmid–Based Biocatalysis: Plasmid Assembly and 3–Deoxy–arabino–heptulosonate Production", JACS, vol. 112, pp. 1657–1659, 1990.
K.M. Draths & J.S. Frost, "Genomic Direction of Synthesis During Plasmid–Based Biocatalysis", JACS, 1990, V. 112, p. 9630.
Stu Borman, "New biosynthehtic route to catechol discovered," C&EN, p. 26, Jan. 6, 1992.
K.M. Draths and J.W. Frost, "Conversion of D–Glucose into Catehol: The Not–So–Common Pathway of Aromatic Biosynthesis", J. Am. Chem. Soc., vol. 113, No. 25, pp. 9361–9363, 1991.
David Brewster, Robin S. Jones and Dennis V. Parke, "Aromatization of Shikimic Acid in the Rat and the Role of Gastrointestinal Micro–Organisms", 562nd Meeting of Biochemical Society Transactions; pp. 518–521,1976.
David Brewster, Robin S. Jones and Dennis V. Parke, "The Metabolism of Shikimate in the Rat", Biochem J. vol. 170, pp. 257–264, 1978.

(List continued on next page.)

*Primary Examiner*—Mindy Fleisher
*Assistant Examiner*—Philip W. Carter
*Attorney, Agent, or Firm*—Barnes & Thornburg

[57] ABSTRACT

A method is provided for synthesizing catechol from a biomass-derived carbon source capable of being used as a host cell having a common pathway of aromatic amino acid biosynthesis. The method comprises the steps of biocatalytically converting the carbon source to 3-dehydroshikimate in said host cell, biocatalytically converting the DHS to protocatechuate, and decarboxylating the protocatechuate to form catechol. Also provided is a heterologous *E. coli* transformant characterized by the expression of genes encoding transhetolase, DAHP synthase, and DHQ synthase, further characterized by the constitutive expression of structural genes encoding 3-dehydroshikimate dehydratase and protocatechuate decarboxylase.

9 Claims, 3 Drawing Sheets

OTHER PUBLICATIONS

Neil C. Bruce and Ronald B. Cain, "Hydroaromatic Metabolism in *Rhodococcus Rhodochrous*: Purification and Characterisation of its NAD-dependent Quinate Dehydrogenase", Archives of Microbiology, vol. 154 pp. 179–186, 1990.

John W. Frost, Judith L. Bender, James T. Kadonaga and Jeremy R. Knowles, "Dehydroquinate Synthase from *Escherichia coli*: Purification, Cloning, and Construction of Overproducers of the Enzyme", Biochemistry, vol. 23, pp. 4470–4475, 1984.

K.M. Draths and J.W. Frost, "Genomic Direction of Synthesis during Plasmid-Based Biocatalysis", Journal of the American Chemical Society, vol. 112, pp. 9630–9632, 1990.

J.L. Canovas, M.L. Whellis, and R.Y. Stanier, "Regulation of the Enzymes of the β–Ketodipate Pathway in *Moraxella calcoacetica*—The Role of Protocatechuate as Inducer", European Journal of Biochemistry, vol. 3, pp. 293–304, 1968.

W.M. Ingledew, M. Elena F. Tresguerres and J.L. Canovas, "Regulation of the Enzymes of the Hydroaromatic Pathway in *Acinetobacter calco-aceticus*", The Journal of General Microbiology, vol. 68, pp. 273–282, 1971.

J. Elena F. Tresguerres, W.M. Ingledew, and J.L. Canovas, "Potential Competition for 5–Dehydroshikimate between the Aromatic Biosynthetic Route and the Catabolic Hydroaromatic Pathway", Arch. Mikrobiol., vol. 82, pp. 111–119, 1972.

Heather K. Lamb, Clive R. Bagshaw, and Alastair R. Hawkins, "In vivo overproduction of the pentafunctional *arom* polypeptide in *Aspergillus nidulans* affects metabolic flux in the quinate pathway", MGG, vol. 227, pp. 187–196, 1991.

R.B. Cain, "The Regulation of Enzymes of Aromatic–Ring Fission in Fungi: Organisms using only the Protocatechuate Pathway", Biochemical Journal vol. 114(4) p. 76, 1969.

R.S. Chaleff, "The Inducible Quinate–Shikimate Catabolic Pathway in *Neurospora Crassa*: Genetic Organization", Journal of General Microbiology, vol. 81 pp. 337–355, 1974.

C. Ratledge, "The Production of an N–Acylanthranilic Acid From Shikimic Acid and the Effect of Iron Deficiency on the Biosynthesis of other Aromatic Compounds By *Aerobacter aerogenes*", Biochimica Et Biophysica Acta, vol. 141 pp. 55–63, 1967.

J.C. Patel and D.J.W. Grant, "The Formation of Phenol in the Degradation of p–hydroxybenzoic acid by *Klebsiella aerogenes (Aerobacter aerogenes)*", Antonie van Leeuwenhoek, vol. 35, pp. 53–64, 1969.

A.J. Pittard, F. Gibson and C.H. Doy, "A Possible Relationship Between The Formation of o–Dihydric Phenols and Tryptophan Biosynthesis by *Aerobactor aerogenes*", Biochimica ET Biophysica Acta, vol. 57, pp. 290–298, 1962.

A.J. Pittard, F. Gibson and C.H. Doy, "Phenolic Compounds Accumulated By Washed Cell Suspensions of a Tryptophan Auxotroph of *Aerobacter aerogenes*", Biochim, Biophys, Acta, vol. 49, pp. 485–494, 1961.

D.J.W. Grant, "The Oxidative Degradation of Benzoate and Catechol by *Klebsiella aerogenes (Aerobacter aerogenes)*", Antonie van Leeuwenhock, vol. 36, pp. 161–177, 1970.

Katsuhisa Shirai, "Catechol Production from Benzene through Reaction with Resting and Immobilized Cells of Mutant Strain of *Pseudomonas*", Agric. Biol. Chem., vol. 51(1), pp. 121–128, 1987.

Katsuhisa Shirai, "Screening of Microorganisms for Catechol Production from Benzene", Agric. Biol. Chem., vol. 50(11) pp. 2875–2880, 1986.

SYNTHESIS OF CATECHOL FROM BIOMASS-DERIVED CARBON SOURCES

BACKGROUND AND SUMMARY OF THE INVENTION

This invention relates to the production of catechol and precursors thereof by the conversion of biomass-derived carbon sources. More particularly this invention is directed to the biocatalytic conversion of glucose, and other sugars capable of being used in the biosynthesis of aromatic amino acids, to catechol by way of 3-dehydroshikimate and protocatechuate.

Catechol is an exceptionally important molecule used as a starting material in the synthesis of pharmaceuticals, pesticides, flavors, fragrances, solar protectants, and polymerization inhibitors. Annual worldwide production exceeds 20,000 metric tons.

Currently, most commercial production of catechol is based on the reaction of phenol with peracids or the metal-catalyzed ($Fe^{+2}$, $Co^{+2}$) reaction of phenol with hydrogen peroxide. Catechol is also produced from the distillation of coal tar. However, these procedures are not entirely desirable given that they use non-renewable, fossil fuel-based starting materials and yield complex mixtures of catechol with aromatic by-products such as hydroquinone. Moreover, these reactions require high temperatures and involve the use of environmentally sensitive materials. Other routes to catechol include alkaline hydrolysis of o-chlorophenol and Fries peroxide rearrangement of salicylaldehyde, but these are no longer commercially viable.

Microbial biosynthesis has also been used for producing catechol, albeit not commercially. Microbial biosynthesis requires the identification of microbes capable of converting starting materials to catechol. Although some such microbes have been identified, the substrates for their biocatalytic activity are benzene or phenol. Benzene, a known carcinogen, poses significant environmental risks. Furthermore, benzene and its derivatives (such as phenol) are produced from fossil fuels, a non-renewable resource. Thus, to date, microbial biosyntheses of catechol have presented no discernible advantage over traditional chemical syntheses from the standpoints of environmental safety and resource consumption.

There are also reports in the literature of the incidental formation of catechol along with other products when certain microbial strains and mutants are cultured in a medium where m-glucose is the carbon source. However, the described strains yield an uncertain and complex mixture produced by way of an undefined biocatalytic pathway.

It would be desirable to provide a synthesis route for catechol which not only avoids reliance on environmentally sensitive starting materials but also makes efficient use of renewable resources. It would further be desirable to provide a synthesis route for catechol which provides catechol as an exclusive product rather than as part of a complex mixture.

The present invention provides methods for the microbial biosynthesis of catechol from readily available carbon sources capable of biocatalytic conversion to D-erythrose 4-phosphate (E4P) and phosphoenolpyruvate (PEP) in microorganisms having a common pathway of aromatic amino acid biosynthesis. One preferred carbon source is D-glucose. Advantageously, D-glucose, and the various other carbon sources useable in connection with the present invention, are non-toxic. Furthermore, they are renewable resources derived from starch, cellulose and sugars found in corn, sugar cane, sugar beets, wood pulp and other biomass resources.

Host microbial organisms suitable for carrying out biosyntheses in accordance with the present invention belong to genera possessing an endogenous common pathway of aromatic amino acid biosynthesis. Preferred host organisms are mutant strains of *Escherichia coli* genetically engineered to express selected genes endogenous to *Klebsiella pneumoniae*. One preferred *E. coli* mutant for use in this invention is *E. coli* AB2834, an auxotrophic mutant which is unable to catalyze the conversion of 3-dehydroshikimate (DHS), an intermediate along the common pathway, into shikimic acid due to a mutation in the aroE locus which encodes shikimate dehydrogenase.

The common pathway of aromatic amino acid biosynthesis produces the aromatic amino acids phenylalanine, tyrosine, and tryptophan in bacteria and plants. The common pathway ends in the branch point molecule chorismate, which is subsequently converted phenylalanine, tyrosine, and tryptophan by three separate terminal pathways.

Approaches for increasing the efficiency of production of the common pathway have been described in U.S. Patent No. 5,168,056 (issued Dec. 1, 1992), and U.S. patent application Ser. No. 07/994,194 filed Dec. 21, 1992, the disclosures of which are expressly incorporated herein by reference.

In using the genetically engineered mutant host organisms to produce catechol according to this invention, carbon flow directed into aromatic amino acid biosynthesis proceeds along the common pathway to yield elevated intracellular levels of the DHS intermediate, which accumulate due to a mutation which prevents conversion of DHS to chorismate along the common pathway. In a pathway diverging from the common pathway, DHS serves as the substrate for the enzyme 3-dehydroshikimate dehydratase to produce protocatechuate which is thereafter converted to catechol with protocatechuate decarboxylase. Preferably these enzymes are constitutively expressed in the host cell as a result of the transformation of the host cell with recombinant DNA comprising genes encoding those enzymes. Carbon flow thereby is forced away from the common pathway into the divergent pathway to produce catechol.

For example, in the host strain *E.coli* AB2834, intracellular concentrations of DHS increase due to a mutation in a gene (aroE) which encodes shikimate dehydrogenase. DHS is transformed to catechol along a divergent pathway enabled by transformation of the host cell with expressible genetic fragments encoding DHS dehydratase and protocatechuate decarboxylase and with genes encoding for enzymes which work to commit an increased amount of carbon to the common pathway of aromatic amino acid biosynthesis. The result is a divergent pathway in which carbon flow originally directed into the common pathway of aromatic amino acid biosynthesis is directed to protocatechuate from DHS, and thereafter to produce catechol from protocatechuate. Analysis of the culture supernatants of recombinant mutants of this invention using nuclear magnetic resonance spectroscopy (NMR) demonstrates that catechol accumulates extracellularly as an exclusive product.

Additional objects, features, and advantages of the invention will become apparent to those skilled in the art upon consideration of the following detailed description of preferred embodiments exemplifying the best mode of carrying out the invention as presently perceived.

DETAILED DESCRIPTION OF THE INVENTION

In accordance with this invention there is provided a method of producing catechol from biomass-derived carbon sources capable of being used by a host cell having a common pathway of aromatic amino acid biosynthesis. In one preferred embodiment, the method comprises biocatalytically converting the carbon source to an intermediate along the common pathway, and then biocatalytically converting the intermediate to catechol by forcing carbon flow away from the common pathway onto a divergent pathway. In the divergent pathway, the intermediate, 3-dehydroshikimate (DHS), is biocatalytically converted to protocatechuate, and the protocatechuate is thereafter decarboxylated to form catechol.

Figure 1A:
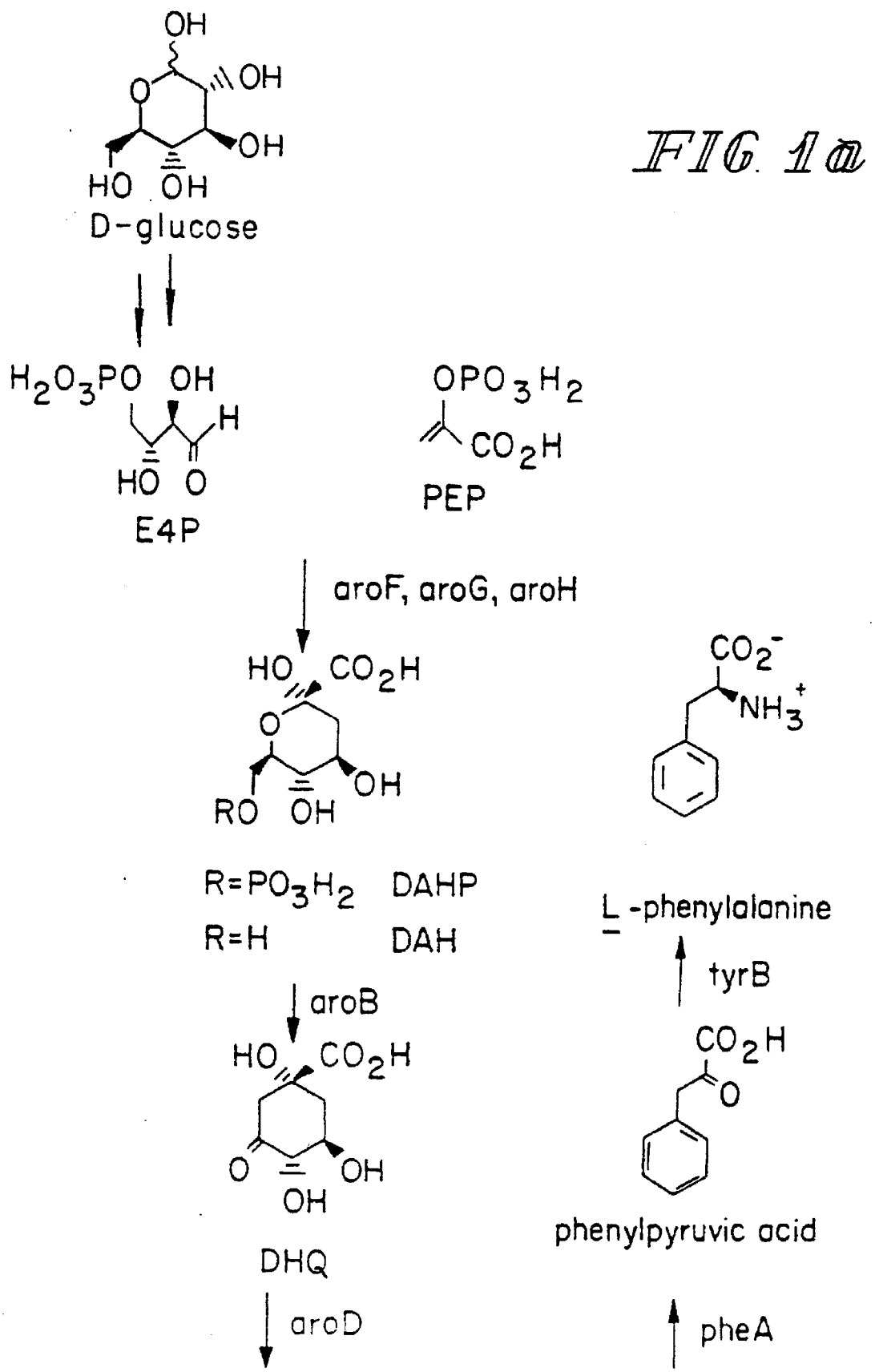
FIG. 1 illustrates the common pathway of aromatic amino acid biosynthesis and the divergent pathway enabling synthesis of catechol from 3-dehydroshikimate.
Figure 1B:
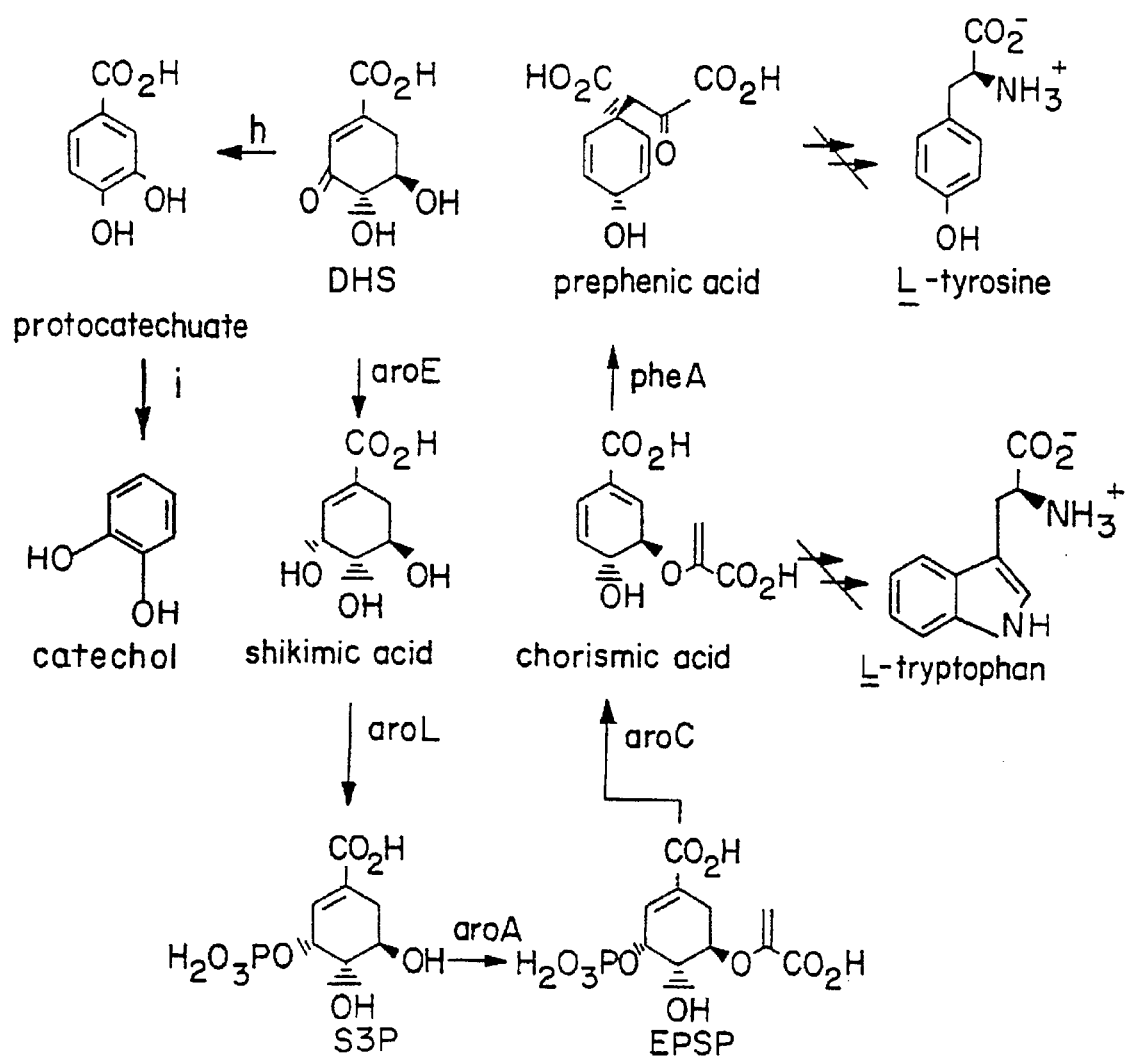

Biomass-derived carbon sources useable in accordance with this invention include any carbon sources capable of being biocatalytically converted into D-erythrose 4-phosphate (E4P) and phosphoenolpyruvate (PEP), two precursor compounds to the common pathway of aromatic amino acid biosynthesis (see FIG. 1). Suitable carbon sources include, but are not limited to, starches, cellulose, and sugar moieties such as glucose, pentoses, and fructose. In preferred embodiments, D-glucose is the carbon source for use by host cells in accordance with the present invention.

Host cells suitable for use in the present invention are members of those genera capable of being utilized for industrial biosynthetic production of desired aromatic compounds. In particular, suitable host cells have an endogenous common pathway of aromatic amino acid biosynthesis. Common aromatic pathways are endogenous in a wide variety of microorganisms, and are used for the production of various aromatic compounds. As illustrated in FIG. 1, the common aromatic pathway leads from E4P and PEP (the availability of E4P being increased by the pentose phosphate pathway enzyme transketolase, encoded by the tkt gene) to chorismic acid with many intermediates in the pathway. The intermediates in the pathway include 3-deoxy-D-arabino-heptulosonic acid 7-phosphate (DAHP), 3-dehydroquinate (DHQ), 3-dehydroshikimate (DHS), shikimic acid, shikimate 3-phosphate (S3P), and 5-enolpyruvoylshikimate-3-phosphate (EPSP). The enzymes in the common pathway, and their respective genes, include DAHP synthase (aroF), DHQ synthase (aroB), DHQ dehydratase (aroD), shikimate dehydrogenase (aroE), shikimate kinase (aroL, aroK), EPSP synthase (aroA) and chorismate synthase (aroC).

Host cells including common pathways of this type include prokaryotes belonging to the genera Escherichia, Klebsiella, Corynebacterium, Brevibacterium, Arthrobacter, Bacillus, Pseudomonas, Streptomyces, Staphylococcus, or Serratia. Eukaryotic host cells can also be utilized, with yeasts of the genus Saccharomyces or Schizosaccharomyces being preferred.

More specifically, prokaryotic host cells are derived from species that include *Escherichia coli, Klebsiella pneumonia, Corynebacterium glutamicum, Corynebacterium herculis, Brevibacterium divaricatum, Brevibacterium lactofermentum, Brevibacterium flavum, Bacillus brevis, Bacillus cereus, Bacillus circulans, Bacillus coagulans, Bacillus lichenformis, Bacillus megaterium, Bacillus mesentericus, Bacillus pumilis, Bacillus subtilis, Pseudomonas aeruginosa, Pseudomonas angulata, Pseudomonas fluorescens, Pseudomonas tabaci, Streptomyces aureofaciens, Streptomyces avermitilis, Streptomyces coelicolor Streptomyces griseus, Streptomyces kasugensis, Streptomyces lavendulae, Streptomyces lipmanii, Streptomyces lividans, Staphylococcus epidermis, Staphylococcus saprophyticus,* or *Serratia marcescens*. Preferred eukaryotic host cells include *Saccharomyces cerevisiae* or *Saccharomyces carlsbergensis*.

In preferred embodiments of the invention, host cells include auxotrophic mutant cell lines having a mutation in the common pathway of amino acid biosynthesis that blocks the conversion of DHS to the branch point molecule, chorismate. Such mutants are unable to catalyze the conversion of 3-dehydroshikimate (DHS) into chorismate due to a mutation in one or more of the genes encoding shikimate dehydrogenase, shikimate kinase, EPSP synthase or chorismate synthase, and will thus accumulate elevated intracellular levels of DHS. Preferred mutant cell lines include *Escherichia coli* strains AB2834, AB2829 and AB2849.

*E. coli* AB2834 is unable to catalyze the conversion of 3-dehydroshikimate (DHS) into shikimic acid due to a mutation in the aroE locus which encodes shikimate dehydrogenase. Use of *E. coli* AB2834 ensures that the carbon flow directed into aromatic amino acid biosynthesis is not processed beyond DHS. Similarly *E. coli* AB2829 (which is unable to catalyze the conversion of shikimate 3-phosphate (S3P) into 5-enolpyruvylshikimate-3-phosphate (EPSP) due to a mutation in the aroA locus which encodes EPSP synthase) and *E. coli* AB2849 (which is unable to catalyze the conversion of EPSP into chorismic acid due to a mutation in the aroC locus which encodes chorismate synthase) also result in increased intracellular levels of DHS. *E. coli* AB2834 is the host cell line used in preferred embodiments.

To be used according to the present invention, host cells of the type described herein are transformed so that the intracellular DHS can be used as a substrate for biocatalytic conversion to catechol. Preferably, host cells are transformed with recombinant DNA to force carbon flow away from the common pathway intermediates normally synthesized from DHS and into a divergent pathway to produce catechol.

The divergent pathway is illustrated in FIG. 1. As shown, the intermediate in the divergent pathway is protocatechuate. The enzyme responsible for the biocatalytic conversion of DHS to protocatechuate is the enzyme 3-dehydroshikimate dehydratase, labelled "h" in FIG. 1, and its gene is aroZ. The enzyme responsible for the decarboxylation of protocatechuate to form catechol is protocatechuate decarboxylase, labelled "i" in FIG. 1, and its gene is aroY. Thus, the recombinant DNA for transforming host cells for use in accordance with the present invention comprises constitutively expressed genes encoding 3-dehydroshikimate dehydratase and protocatechuate decarboxylase.

The enzymes 3-dehydroshikimate dehydratase and protocatechuate decarboxylase were recruited from the ortho cleavage pathways which enable microbes such as Neurospora, Aspergillus, Acinetobacter, Klebsiella, and Pseudomonas to use aromatics (benzoate and p-hydroxybenzoate) as well as hydroaromatics (shikimate and quinate) as sole sources of carbon for growth. DHS dehydratase plays a critical role in microbial catabolism of quinic and shikimic acid. Protocatechuate decarboxylase was formulated by Patel to catalyze the conversion of protocatechuate into catechol during catabolism of p-hydroxybenzoate by *Klebsiella aerogenes*. Reexamination of Patel's strain (now referred to as *Enterobacter aerogenes*) [(a) Grant, D. J. W.; Patel, J. C. Antonie van Leewenhoek 1969, 35, 325. (b) Grant, D. J. W. Antonie van Leewenhoek 1970, 36, 161] recently led Ornston to conclude that protocatechuate decarboxylase was not metabolically significant in catabolism of p-hydroxybenzoate [Doten, R. C.; Ornston, N. *J. Bacteriol.* 1987, 169, 5827]. The true role of protocatechuate decarboxylase in ortho cleavage is thus something of an enigma.

The mechanism for transforming the host cell to direct carbon flow into the divergent pathway preferably involves the insertion of genetic elements including expressible sequences coding for 3-dehydroshikimate dehydratase and protocatechuate decarboxylase. Regardless of the exact mechanism utilized, it is contemplated that the expression of these enzymatic activities will be effected or mediated by the transfer of recombinant genetic elements into the host cell. Genetic elements as herein defined include nucleic acids (generally DNA or RNA) having expressible coding sequences for products such as proteins, apoproteins, or antisense RNA, which can perform or control pathway enzymatic functions. The expressed proteins can function as enzymes, repress or derepress enzyme activity, or control expression of enzymes. The nucleic acids coding these expressible sequences can be either chromosomal (e.g. integrated into a host cell chromosome by homologous recombination) or extrachromosomal (e.g. carried by plasmids, cosmids, etc).

The genetic elements of the present invention can be introduced into a host cell by plasmids, cosmids, phages, yeast artificial chromosomes or other vectors that mediate transfer of the genetic elements into a host cell. These vectors can include an origin of replication along with cis-acting control elements that control replication of the vector and the genetic elements carried by the vector. Selectable markers can be present on the vector to aid in the identification of host cells into which the genetic elements have been introduced. For example, selectable markers can be genes that confer resistance to particular antibiotics such as tetracycline, ampicillin, chloramphenicol, kanamycin, or neomycin.

A preferred means for introducing genetic elements into a host cell utilizes an extrachromosomal multi-copy plasmid vector into which genetic elements in accordance with the present invention are inserted. Plasmid borne introduction of the genetic element into host cells involves an initial cleaving of a plasmid with a restriction enzyme, followed by ligation of the plasmid and genetic elements in accordance with the invention. Upon recircularization of the ligated recombinant plasmid, transduction or other mechanism (e.g., electroporation, microinjection, etc.) for plasmid transfer is utilized to transfer the plasmid into the host cell. Plasmids suitable for insertion of genetic elements into the host cell include but are not limited to pBR322, and its derivatives such as pAT153, pXf3, pBR325, pBr327, pUC vectors, pACYC and its derivatives, pSC101 and its derivatives, and ColE1. In addition cosmid vectors such as pLAFR3 are also suitable for the insertion of genetic elements into host cells. Preferred plasmid constructs include but are not limited to p2-47, pKD8.243A, pKD8.243B, and pSUaroZY157-27, which carry the aroZ and aroY loci isolated from *Klebsiella pneumoniae* which respectively encode 3-dehydroshikimate dehydratase and protocatechuate decarboxylase.

Typically, the mechanism for transforming host cells in accordance with the present invention will also include insertion of genes encoding for enzymes which increase commitment of carbon into the common pathway of aromatic amino acid biosynthesis. The expression of a gene is primarily directed by its own promoter, although other genetic elements including optional expression control sequences such as repressors, and enhancers can be included to control expression or derepression of coding sequences for proteins, apoproteins, or antisense RNA. In addition, recombinant DNA constructs can be generated whereby the gene's natural promoter is replaced with an alternative promoter to increase expression of the gene product. Promoters can be either constitutive or inducible. A constitutive promoter controls transcription of a gene at a constant rate during the life of a cell, whereas an inducible promoter's activity fluctuates as determined by the presence (or absence) of a specific inducer. For example, control sequences can be inserted into wild type host cells to promote overexpression of selected enzymes already encoded in the host cell genome, or alternatively can be used to control synthesis of extrachromosomally encoded enzymes.

In the present invention, control sequences to promote overproduction of DHS are preferably used. As previously noted, DHS is synthesized in the common pathway by the sequential catalytic activities of the tyrosine-sensitive isozyme of 3-deoxy-D-arabino-heptulosonic acid 7-phosphate (DAHP) synthase (encoded by aroF) and 3-dehydroquinate (DHQ) synthase (encoded by aroB) along with the pentose phosphate pathway enzyme transketolase (encoded by tkt). The expression of these biosynthetic enzymes can be amplified to increase the conversion of D-glucose into DHS. Increasing the in vivo catalytic activity of DAHP synthase, the first enzyme of the common pathway, increases the flow of D-glucose equivalents directed into aromatic biosynthesis. However, levels of DAHP synthase catalytic activity are reached beyond which no further improvements are achieved in the percentage of D-glucose which is committed to aromatic biosynthesis. At this limiting level of aromatic amino acid biosynthesis, amplification of the catalytic levels of the pentose phosphate pathway enzyme transketolase achieves sizable increases in the percentage of D-glucose siphoned into the pathway.

Amplified transketolase activity has been suggested to increase D-erythrose 4-phosphate concentrations. As one of the two substrates for DAHP synthase, limited D-erythrose 4-phosphate availability likely limits DAHP synthase catalytic activity. One preferred means of amplifying the catalytic activities of DAHP synthase, DHQ synthase and DHQ dehydratase is to overexpress the enzyme species by transforming the host cell with a recombinant DNA sequence encoding these enzymes.

Amplified expression of aroF-encoded DAHP synthase and tkt-encoded transketolase creates a surge of carbon flow directed into the common pathway of aromatic amino acid biosynthesis which is in excess of the normal carbon flow directed into this pathway. If the individual rates of conversion of substrate into product catalyzed by individual common pathway enzymes are not similar to the rate of DAHP synthesis, the substrates of these rate-limiting enzymes will accumulate intracellularly.

Microbial organisms such as *E. coli* frequently cope with accumulated substrates by exporting such substrates into the growth supernatant. This results in a loss of carbon flow through the common pathway since exported substrates are typically lost to the microbe's metabolism. DHQ synthase is a example of a rate-limiting common pathway enzyme. Amplified expression of DHQ synthase removes the rate-limiting character of this enzyme, and prevents the accumulation of DAHP and its nonphosphorylated analog, DAH. DHQ dehydratase is not rate-limiting. Therefore, amplified expression of aroF-encoded DAHP synthase, tkt-encoded transketolase and aroB-DHQ synthase increases production of DHS, which in the presence of DHS dehydratase and protocatechuate decarboxylase is converted to catechol. The synthesized catechol will then accumulate as an end product and subsequently be exported into the growth medium.

One particularly preferred plasmid for promoting the efficiency of carbon flow along the common pathway between the carbon source and DHS is plasmid pKD136, which encodes the aroF, tkt and aroB genes. Plasmid pKD136 directs the surge of carbon flow into aromatic biosynthesis due to amplified expression of DAHP synthase (encoded by aroF) and transketolase (encoded by tkt). This surge of carbon flow is then delivered intact into DHS synthesis by pKD136 due to amplified expression of DHQ synthase (encoded by aroB).

Thus, in accordance with one preferred embodiment of the present invention, a heterologous strain of *Escherichia coli* expressing genes encoding DHS dehydratase and protocatechuate decarboxylase has been constructed enabling the biocatalytic production of catechol from D-glucose. Efficient conversion of D-glucose to DHS was accomplished upon transformation of the host cell with pKD136. The strain *E. coli* AB2834/pKD136 was then transformed with plasmid p2-47. The end result was *E. coli* AB2834/pKD136/p2-47, a heterologous microbe which catalyzes the conversion of D-glucose into catechol.

The present invention thus relates to a method for producing catechol in a host cell having a common pathway of aromatic amino acid biosynthesis. The method comprises the steps of transforming the host cell with recombinant DNA to create a heterologous host cell. The recombinant DNA comprises constitutively express genes encoding 3-dehydroshikimate dehydratase and protocatechuate decarboxylase, and culturing the transformed host cell in a medium containing a carbon source. In one aspect of this invention, the host cell is further transformed with recombinant DNA comprising sequences encoding the enzyme species transketolase, DAHP synthase, and DHQ synthase. In another preferred aspect, the host cell is selected from the group consisting of mutations which block the synthesis of intermediates in the pathway downstream of DHS. One such host cell is *E. coli* strain aroE.

In another preferred embodiment, the present invention comprises recombinantly transformed *E. coli*. strains selected from the group consisting of *E. coli* AB2834/pKD136/p2-47, *E. coli* AB2834/pKD136/pKD8.243A and *E. coli* AB2834/pKD136/pKD8.243B. Bacterial cell line AB2834pKD136/pKD8.243A, which expresses the enzyme species 3-dehydroshikimate dehydratase and protocatechuate decarboxylase, was deposited with the American Type Culture Collection, 12301 Parklawn Drive, Rockville Md. 20852, on Mar. 19, 1996 and assigned accession number 98014. In a further preferred embodiment, the invention comprises recombinant plasmid constructs selected from the group consisting of p2-47, pKD8.243A and pKD8.243B.

EXAMPLE 1

Isolation of the aroZ gene from *Klebsiella pneumoniae*

Isolation of the gene which encodes DHS dehydratase (designated aroZ for purposes of the present description) began with purification of genomic DNA from *Klebsiella pneumoniae* strain A170-40. Partial digestion of genomic DNA with BamH I was used to produce fragments in the range of 15 kb to 30 kb. The resulting DNA fragments were ligated to pLAFR3 which had previously been digested with BamH I and subsequently treated with calf intestinal alkaline phosphatase. pLAFR3 is a tetracycline resistant cosmid possessing the RK2 replicon. Packagene Packaging System (Promega) was used to package the ligated DNA, and the resulting phage particles were used to infect *E. coli* DH5α/pKD136. Plasmid pKD136 is a pBR325-based vector (pMB1 origin of replication) containing genes which encode transketolase (tkt), DAHP synthase (aroF), and DHQ synthase (aroB) as well as an ampicillin resistance gene. Colonies which were resistant to both tetracycline and ampicillin were subsequently plated onto chromogenic minimal medium (M9) plates containing D-glucose (4 g $L^{-1}$), shikimic acid (0.04 g $L^{-1}$), ferric citrate (0.07 g $L^{-1}$), p-toluidine (1.9 g $L^{31\ 1}$), ampicillin (0.05 g $L^{-1}$), and tetracycline (0.013 g $L^{-1}$). After incubation at 37° C. for 48 h, the growth medium surrounding colony 5-87 appeared slightly brown in color. Continued incubation at room temperature resulted in further darkening of the agarose surrounding colony 5-87. The DNA which was purified from a culture of colony 5-87 consisted of pKD136 and a tetracycline resistant plasmid referred to as p5-87.

Digestion of plasmid p5-87 with BamH I followed by agarose gel electrophoresis produced five DNA fragments which were detectable by ethidium staining. The 22 kb band represented the pLAFR3 host vector while the 5.7 kb, 4.3 kb, 3.5 kb, and 0.5 kb fragments represented the aroZ encoding *Klebsiella pneumoniae* insert. The resulting BamH I fragments were ligated into pLAFR3 which had previously been digested with BamH I and treated with phosphatase. Following transformation of the ligation products into DH5α/pKD136, the resulting ampicillin and tetracycline resistant colonies were screened as described above for the ability to turn minimal medium agarose plates containing p-toluidine and ferric citrate brown. Using this technique, plasmid p4-20 was isolated which contained the 3.5 kb BamH I fragment.

In an effort to minimize the size of the aroZ-encoding insert, plasmid p5-87 was digested with BamH I and the resulting fragments were ligated to vector pSU19 which had previously been digested with BamH I and treated with phosphatase. Plasmid pSU19 contains the p15A replicon and the gene which imparts resistance to chloramphenicol. Following transformation of the ligation products into *E. coli* DH5 α/pKD136, the resulting ampicillin and chloramphenicol resistant colonies were screened as described in Example 1 for the ability to turn chromogenic minimal medium agarose plates containing p-toluidine and ferric citrate brown. Using this technique, plasmid pSU1-31 was isolated which consisted of a 3.5 kb BamH I insert contained in pSU19.

EXAMPLE 2

Confirmation of the cloning of aroZ

Confirmation that both plasmid p5-87 and pSU1-31 contain the aroZ gene relied on the fact that transformation of an *E. coli* strain which typically converts D-glucose into DHS could further convert DHS into protocatechuic acid. *E. coli* AB2834 accumulates DHS in the culture supernatant due to a mutation in the aroE gene, which encodes shikimate dehydrogenase. Conversion of D-glucose to DHS is maximized when AB2834 is transformed with pKD136. AB2834 was co-transformed with pKD136 and p5-87 to produce colonies which were resistant to both ampicillin and tetracycline. One liter of LB medium (4 L Erlenmeyer flask) was inoculated with an overnight culture (5 mL) of AB2834/pKD136/p5-87. The culture was grown at 37° C. for 8 h with agitation (250 rpm). The cells were then harvested and resuspended in one liter (4 L Erlenmeyer flask) of minimal M9 medium containing glucose (10 g L$^{-1}$), shikimic acid (0.04 g L$^{-1}$), ampicillin (0.05 g L$^{-1}$), and tetracycline (0.013 g L$^{-1}$). The culture was returned to 37° C. incubation. Aliquots of the culture were removed after 24 h and 64 h and centrifuged to remove cells. Five milliliters of isolated supernatant was collected from each sample and the water was removed in vacuo. Samples were redissolved in D$_2$O and concentrated in vacuo. Repetition of this procedure resulted in exchange of residual water with D$_2$O and samples suitable for analysis by $^1$H NMR. Using the sodium salt of 3-(trimethylsilyl)propionic 2,2,3,3-d$_4$ acid as an internal standard, it was determined that approximately 9 mM protocatechuic acid had accumulated in the culture supernatant. Diagnostic resonances at δ6.94 (d, 7 Hz, 1H) and δ7.48 (d, 7 Hz, 2H) were indicative of protocatechuic acid. DHS was not detected in the culture supernatant. It was concluded from this experiment that the gene which encodes DHS dehydratase was localized on plasmid p5-87.

When AB2834/pKD136/pSU1-31 was grown on a 1 L scale under conditions similar to those described immediately above, $^1$H NMR analysis of the culture supernatant of indicated that 11 mM protocatechuic acid accumulated extracellularly. It was concluded from this experiment that the aroZ gene had been successfully subcloned and was localized on plasmid pSU1-31.

EXAMPLE 3

Isolation of the aroY gene from *Klebsiella pneumoniae*

At this point the aroZ gene had been isolated on a 3.5 kb BamH I fragment localized in both p4-20 (pLAFR3 vector) and pSU1-31 (pSU19 vector). DH5α/pKD136/p4-20 colonies were shown to impart a local brown coloration when grown on minimal medium agarose plates containing ferric citrate and p-toluidine. Selection of a plasmid containing the gene which encodes protocatechuate decarboxylase (designated aroY for purposes of the present description) relied on the fact that expression of protocatechuate decarboxylase in DH5α/pKD136/p4-20 was expected to produce quantities of catechol rather than protocatechuate. Since catechol reacts with p-toluidine to give a more intense brown color than does protocatechuate, it was expected that a colony producing catechol could be selected from a background of colonies producing protocatechuate when scored on chromogenic minimal medium (M9) plates.

Isolation of a plasmid containing the aroY gene began with partial digestion of *K. pneumoniae* genomic DNA with EcoR I to produce fragments ranging in size from 15 kb to 30 kb. The resulting fragments were ligated into cosmid p4-20 which had previously been digested with EcoR I and treated with phosphatase. Ligated DNA was packaged in lamba phage heads which were then used to infect DH5α/pKD136. Resulting colonies that were both ampicillin and tetracycline resistant were screened on minimal medium agarose plates which contained p-toluidine and ferric citrate. After incubation at 37° C. for approximately 24 h, colony 2-47 was producing a local region of brown that was lacking from all other colonies.

Isolation of DNA from colony 2-47 yielded plasmid pKD136 and plasmid p2-47 which were subsequently co-transformed into competent cells to yield *E. coli* AB2834/pKD136/p2-47.

Similar to the original strategy for isolation of the DNA encoding protocatechuate decarboxylase, subcloning of the aroY EcoR I fragment to its minimal size also relied on synthesis of catechol by an aroE host strain in the presence of DHS dehydratase. Digestion of p2-47 to completion with EcoR I indicated that the aroY insert consisted of two EcoR I fragments of approximately 8 kb and 11.9 kb. Localization of the 11.9 kb EcoR I fragment in pSU1-31 yielded plasmid pSUaroZY157-27.

Figure 2:
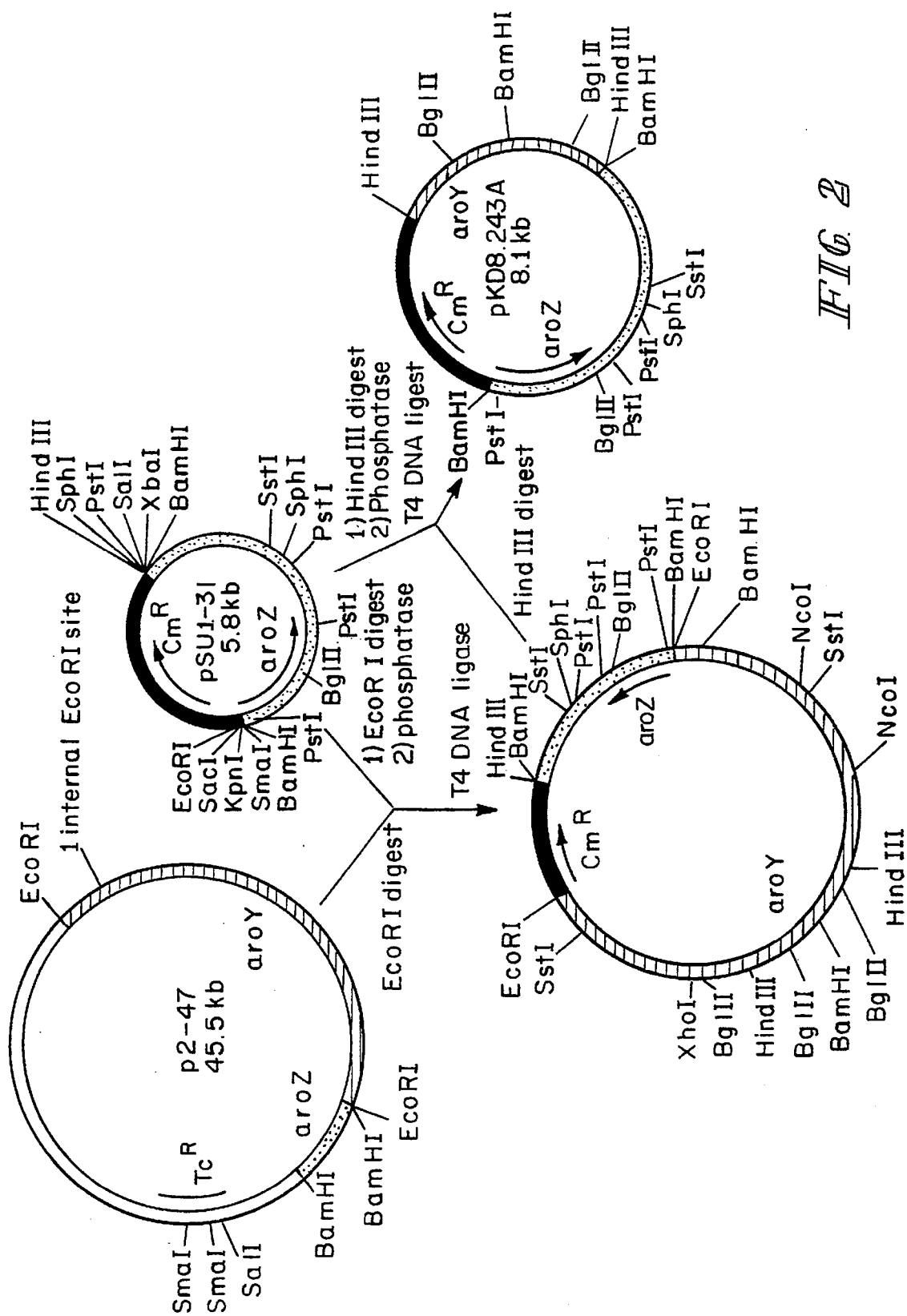
FIG. 2 presents a plasmid map of p2-47 and illustrates how plasmid pKDS.243A was generated from plasmids p2-47, pSU1-31, and pSUaroZY 157-27.

Mapping of the 11.9 kb EcoR I fragment in conjunction with further subcloning indicated that the aroY gene was likely located near the middle of the 11.9 kb fragment. Digestion of pSUaroZY157-27 with Hind III produced a 2.3 kb Hind III fragment which was inserted into pSU1-31, yielding plasmid pKD8.243A (FIG. 2). Plasmid pKDS8.243B was also isolated in which the 2.3 kb Hind III fragment is in the opposite orientation relative to the vector.

EXAMPLE 4

Biocatalytic Conversion of DHS to Protocatechuate by Plasmid p5-87

Co-transformation of pKD136 and p5-87 into *E. coli* AB2834 yielded ampicillin and tetracycline resistant AB2834/pKD136/p5-87. A mutation in the aroE gene of *E. coli* AB2834 renders shikimate dehydrogenase inactive. One liter of LB medium containing ampicillin and tetracycline (4 L Erlenmeyer flask) was inoculated with an overnight culture (5 mL) of AB2834/pKD136/p5-87. The culture was grown at 37° C. for 8 h with agitation (250 rpm). The cells were then harvested and resuspended in one liter (4 L Erlenmeyer flask) of minimal M9 medium containing glucose (10 g L$^{-1}$), shikimic acid (0.04 g L$^{-1}$), ampicillin (0.05 g L$^{-1}$), and tetracycline (0.013 g L$^{-1}$). The culture was returned to 37° C. incubation. Aliquots of the culture were removed after 24 h and 64 h and centrifuged to remove cells. Five milliliters of isolated supernatant was collected from each sample and the water was removed in vacuo. Samples were redissolved in D$_2$O and concentrated in vacuo. Repetition of this procedure resulted in exchange of residual water with D$_2$O and samples suitable for analysis by $^1$H NMR. Using the sodium salt of 3-(trimethylsilyl)propionic-2,2,3,3-d$_4$ acid as an internal standard, it was determined that approximately 9 mM protocatechuic acid had accumulated in the culture supernatant. Diagnostic resonances at δ6.94 (d, 7 Hz, 1H) and δ7.48 (d, 7 Hz, 2H) were indicative of protocatechuic acid. Additional resonances correspond to unmetabolized D-glucose and acetic acid. DHS was not detected in the culture supernatant. It was concluded from this experiment that the gene which encodes DHS dehydratase was localized on plasmid p5-87.

EXAMPLE 5

Biocatalytic Conversion of DHS to Protocatechuate by Plasmid p4-20

A culture supernatant of AB2834/pKD136/p4-20 was prepared and analyzed as described in example 4. $^1$H NMR analysis indicated that 11 mM protocatechuic acid accumulated extracellularly. Except for acetate (δ1.9, s, 3H), no other products of significant concentration were detected in the culture supernatant.

EXAMPLE 6

Enzymatic Activity of the Subcloned aroZ Gene Construct

The 3.5 kb aroZ encoding BamH I fragment was also cloned into the BamH I site of plasmid pSU19 to produce plasmids pSU1-31 and pSU1-28. Plasmid pSU19 contains the p15A replicon and the gene which imparts resistance to chloramphenicol. A lac promoter is positioned in pSU19 upstream from the multiple cloning site. The only difference between plasmids pSU1-31 and pSU1-28 is the orientation of the BamH I insert relative to the lac promoter.

As further verification that the 3.5 kb BamH I fragment encoded the aroZ gene, cell extracts were assayed for DHS dehydratase activity. In 2 L Erlenmeyer flasks, 500 mL portions of LB containing chloramphenicol (0.02 g L$^{-1}$) were inoculated with 5 mL cultures of DH5α/pSU1-31 or DH5α/pSU1-28. Cells were grown at 37° C. for 12 h with agitation (250 rpm). For each strain, one culture was grown in the presence of 0.2 mM isopropyl β-D-thiogalactoside (IPTG) while a second culture was grown in the absence of IPTG. Cells were harvested and resuspended in 250 mL of Buffer A (100 mM Tris HCl, 2.5 mM MgCl$_2$, pH7.5). The cells were harvested a second time and then resuspended in 2 mL of Buffer A per gram of cellular wet weight. After disruption via French press, the lysate was centrifuged (35,000 g, 30 min, 4° C.) to remove particulate debris. Protein concentrations were determined using the Bradford dye-binding procedure with assay solution purchased from Bio-Rad.

DHS dehydratase was assayed as described by Strøman with the following modifications. The assay solution (1 mL) contained Tris HCl (100 mM), MgCl$_2$ (25 mM), and a aliquot of cellular lysate. The solution was incubated at room temperature and the absorbance at 290 nm was monitored until a stable baseline was achieved. DHS (final concentration 1 mM) was added and the reaction monitored at 290 nm for approximately 20 min. One unit of DHS dehydratase activity was defined as the formation of 1 μmol of protocatechuate (ε=3890 L mol$^{-1}$ cm$^{-1}$) per minute. The likely orientation of the aroZ gene on the BamH I fragment has been determined based on the DHS dehydratase activities (Table 1) obtained in the presence and absence of IPTG for DH5α/pSU1-31 and DH5α/pSU1-28. The fact that pSU1-28 results in higher DHS dehydratase activity likely indicates that the aroZ gene is transcribed from the vector encoded lac promoter as well as from its native K. pneumoniae promoter in this plasmid construct. Addition of IPTG to the growth medium fails to yield elevated DHS dehydratase activity perhaps because the lac promoter is not repressed to a significant extent in DH5α/pSU1-28.

TABLE 1

DHS dehydratase activity of aroZ subclones.

| Strain | Growth Conditions −/+ IPTG (0.2 mM) | DHS dehydratase specific activity (units/mg) |
|---|---|---|
| DH5α/pSU1-28 | − | 0.036 |
| DH5α/pSU1-28 | + | 0.029 |
| DH5α/pSU1-31 | − | 0.018 |
| DH5α/pSU1-31 | + | 0.023 |

EXAMPLE 7

Biocatalytic Conversion of D-Glucose to Catechol Using Plasmid pSUaroZY157-27

A culture supernatant of AB2834/pKD136/pSUaroZY157-27 was prepared and analyzed as described in example 4. $^1$H NMR analysis of the culture supernatant of E. coli AB2834/pKD136/pSUaroZY157-27 accumulated 16 mM catechol in the culture supernatant when supplied with 56 mM D-glucose.

EXAMPLE 8

Biocatalytic Conversion of D-glucose to Catechol Using Plasmid p2-47

A culture supernatant of AB2834/pKD136/p2-47 was prepared and analyzed as described in example 4. $^1$H NMR analysis of the culture supernatant of AB2834/pKD136/p2-47 indicated that after 48 h in minimal medium, the original 56 mM D-glucose supplied to the cell was replaced by 20 mM catechol.

EXAMPLE 9

Biocatalytic Conversion of D-Glucose to Catechol Using Plasmids pKD8.243A and pKD8.243B Plasmids pKD8.243A and pKD8.243B were each co-transformed into AB2834 with plasmid pKD136. When grown on a 1 L scale under conditions similar to those described in example 4, AB2834/pKD136/pKD8.243A synthesized 16 mM catechol from 56 mM D-glucose within 48 h whereas AB2834/pKD136/pKD8.243B synthesized 10 mM catechol. Protocatechuic acid (<4 mM) was also detected in some of the culture supernatants, though not on a consistent basis and not always at the end of the microbial synthesis.

Although the invention has been described in detail with reference to certain preferred embodiments, variations and modifications exist within the scope and spirit of the invention as described and defined in the following claims.

We claim:

1. A method for producing catechol, said method comprising the step of culturing a prokaryotic host cell belonging to the genera Escherichia or Klebsiella, which converts a carbon source to 3-dehydroshikimate by enzymes in the common pathway of aromatic amino acid biosynthesis endogenous to said host cell and further characterized by the expression of heterologous genes encoding 3-dehydroshikimate dehydratase and protocatechuate decarboxylase, in a medium containing said carbon source wherein the carbon source is converted biocatalytically to catechol at a rate greater than 0.21 millimoles/liter/hour.

2. The method of claim 1, wherein the prokaryotic host cell is further characterized by the enhanced expression of genes encoding the enzyme species transketolase, 3-deoxy-D-arabino-heptulosonate 7-phosphate synthase and 3-dehydroquinate synthase.

3. The method of claim 1, wherein the prokaryotic host cell is further characterized by at least one genetic mutation which prevents biocatalytic conversion of 3-dehydroshikimate to chorismate.

4. The method of claim 3, wherein the prokaryotic host cell is *E. coli* strain AB2834.

5. The method of claim 4, wherein the prokaryotic host cell is transformed with plasmid pKD136.

6. A method for producing catechol biocatalytically, said method comprising the step of culturing a prokaryotic host cell belonging to the genera Escherichia or Klebsiella, which converts a carbon source to 3-dehydroshikimate by enzymes in the common pathway of aromatic amino acid biosynthesis endogenous to said host cell, transformed with heterologous genes which express the enzyme species 3-dehydroshikimate dehydratase and protocatechuate decarboxylase, in the presence of a carbon source to produce catechol at a rate greater than 0.21 millimoles/liter/hour.

7. The method of claim 6, wherein the carbon source is D-glucose.

8. The method of claim 6, wherein the structural genes encoding the enzyme species 3-dehydroshikimate dehydratase and protocatechuate decarboxylase are endogenous to *Klebsiella pneumoniae*.

9. The method of claim 6, wherein the prokaryotic host cell is further characterized by at least one genetic mutation which prevents biocatalytic conversion of 3-dehydroshikimate to chorismate.

* * * * *